US009999686B2

(12) United States Patent
Hier et al.

(10) Patent No.: US 9,999,686 B2
(45) Date of Patent: Jun. 19, 2018

(54) DENTAL CLEANING COMPOSITION

(71) Applicant: SLH Optimal Health LLC, Boca Raton, FL (US)

(72) Inventors: Lawrence A. Hier, Boca Raton, FL (US); Ben Vaziri, Mount Prospect, IL (US)

(73) Assignee: SLH Optimal Health LLC, Boca Raton, FL (US)

( * ) Notice: Subject to any disclaimer, the term of this patent is extended or adjusted under 35 U.S.C. 154(b) by 0 days. days.

(21) Appl. No.: 14/427,565

(22) PCT Filed: Sep. 11, 2013

(86) PCT No.: PCT/US2013/059135
§ 371 (c)(1),
(2) Date: Mar. 11, 2015

(87) PCT Pub. No.: WO2014/043163
PCT Pub. Date: Mar. 20, 2014

(65) Prior Publication Data
US 2015/0217001 A1 Aug. 6, 2015

Related U.S. Application Data

(60) Provisional application No. 61/699,640, filed on Sep. 11, 2012.

(51) Int. Cl.
| | | |
|---|---|---|
| *A61K 8/00* | (2006.01) |
| *A61Q 11/00* | (2006.01) |
| *A61K 8/02* | (2006.01) |
| *A61K 49/00* | (2006.01) |
| *A61K 33/16* | (2006.01) |
| *A61K 8/46* | (2006.01) |
| *A61K 8/97* | (2017.01) |

(52) U.S. Cl.
CPC ......... *A61K 49/0004* (2013.01); *A61K 8/466* (2013.01); *A61K 8/97* (2013.01); *A61K 33/16* (2013.01); *A61Q 11/00* (2013.01); *A61K 2800/42* (2013.01)

(58) Field of Classification Search
CPC ......... A61K 8/466; A61K 8/97; A61K 33/16; A61K 2800/42; A61Q 11/00
USPC .............................. 424/9.71, 49, 52, 401, 58
See application file for complete search history.

(56) References Cited

U.S. PATENT DOCUMENTS

| | | | |
|---|---|---|---|
| 3,105,798 A | 10/1963 | Holliday et al. |
| 3,309,274 A | 3/1967 | Herbert |
| 3,490,866 A | 1/1970 | Muhler |
| 3,538,230 A | 11/1970 | Pader et al. |
| 3,549,677 A | 12/1970 | Griebstein et al. |
| 3,577,521 A | 5/1971 | Scheller et al. |
| 3,624,219 A | 11/1971 | Perlitsh |
| 3,723,613 A | 3/1973 | Block et al. |
| 3,967,563 A | 7/1976 | Wason |
| 3,988,162 A | 10/1976 | Wason |
| 3,997,658 A | 12/1976 | Block et al. |
| 4,064,229 A | 12/1977 | Block et al. |
| 4,122,161 A | 10/1978 | Wason |
| 4,153,680 A | 5/1979 | Seybert |
| 4,302,439 A | 11/1981 | Selwyn |
| 4,303,641 A | 12/1981 | Dewolf et al. |
| 4,348,378 A * | 9/1982 | Kosti ................ A61K 8/11 |
| | | | 424/49 |
| 4,420,312 A | 12/1983 | Wason |
| 4,431,628 A | 2/1984 | Gaffar |
| 4,459,277 A | 7/1984 | Kosti |
| 4,517,172 A | 5/1985 | Southard |
| 4,590,061 A | 5/1986 | Southard |
| 4,618,488 A | 10/1986 | Maeyama et al. |
| 4,632,826 A | 12/1986 | Ploeger et al. |
| 4,666,700 A | 5/1987 | Frysh |
| 4,992,251 A | 2/1991 | Aldcroft et al. |
| 4,992,256 A | 2/1991 | Skaggs et al. |
| 5,035,879 A | 7/1991 | Aldcroft et al. |
| 5,098,691 A | 3/1992 | Simone et al. |
| 5,098,695 A | 3/1992 | Newton et al. |
| 5,124,143 A | 6/1992 | Muehlemann et al. |
| 5,190,743 A | 3/1993 | Simone et al. |
| 5,326,554 A * | 7/1994 | Fitz, Jr. .............. A61K 8/19 |
| | | | 424/49 |
| 5,419,888 A | 5/1995 | McGill et al. |

(Continued)

FOREIGN PATENT DOCUMENTS

| | | |
|---|---|---|
| EP | 1 279 703 A1 | 1/2003 |
| JP | H08-509239 A | 10/1996 |

(Continued)

OTHER PUBLICATIONS

Disilvestro et al., Pomegranate extract mouth rinsing effects on saliva measures relevant to gingivitis risk. Phytother Res. Aug. 2009;23(8):1123-7. doi: 10.1002/ptr.2759.
U.S. Appl. No. 14/977,611, filed Dec. 21, 2015, Hier et al.
U.S. Appl. No. 13/013,441, filed Jan. 25, 2011, Hier.
U.S. Appl. No. 13/358,457, filed Jan. 25, 2012, Hier et al.
International Search Report and Written Opinion for PCT/US2012/022617 dated May 25, 2012.
International Preliminary Report on Patentability for PCT/US2012/022617 dated Aug. 8, 2013.
International Search Report and Written Opinion for PCT/US2013/059135 dated Nov. 29, 2013.

(Continued)

*Primary Examiner* — Lezah Roberts
(74) *Attorney, Agent, or Firm* — Wolf, Greenfield & Sacks, P.C.

(57) ABSTRACT

The present invention relates to oral compositions for identifying plaque comprising a dental disclosing agent composition for revealing the presence of dental plaque in a person's mouth. The composition comprises a natural colorant derived from annatto seed and a colorant that stains plaque and when added to annatto seed extract results in a color having a wave length of 500 nm to 580 nm and.

13 Claims, No Drawings

(56) References Cited

U.S. PATENT DOCUMENTS

| | | | |
|---|---|---|---|
| 5,647,903 | A | 7/1997 | McGill et al. |
| 5,891,421 | A | 4/1999 | McGill et al. |
| 6,245,321 | B1 | 6/2001 | Nelson et al. |
| 6,881,430 | B2 | 4/2005 | Kohler et al. |
| 7,182,935 | B2 | 2/2007 | Ribeiro et al. |
| 8,206,738 | B2 | 6/2012 | Singh et al. |
| 8,481,059 | B2 | 7/2013 | Cleary et al. |
| 8,541,021 | B2 | 9/2013 | Singh et al. |
| 2003/0082281 | A1 | 5/2003 | Kohler et al. |
| 2003/0152528 | A1 | 8/2003 | Singh et al. |
| 2003/0170308 | A1 | 9/2003 | Cleary et al. |
| 2003/0235549 | A1 | 12/2003 | Singh et al. |
| 2004/0002132 | A1* | 1/2004 | Ribeiro de Nazare .. C12Q 1/04 435/34 |
| 2004/0105834 | A1 | 6/2004 | Singh et al. |
| 2004/0258723 | A1 | 12/2004 | Singh et al. |
| 2005/0113510 | A1 | 5/2005 | Feldstein et al. |
| 2005/0215727 | A1 | 9/2005 | Feldstein et al. |
| 2007/0237726 | A1 | 10/2007 | White et al. |
| 2009/0131437 | A1 | 5/2009 | Furet et al. |
| 2009/0214451 | A1 | 8/2009 | Canham |
| 2009/0258060 | A1 | 10/2009 | Cleary et al. |
| 2009/0298952 | A1 | 12/2009 | Brimmer et al. |
| 2010/0034871 | A1 | 2/2010 | Mikkelsen et al. |
| 2010/0239644 | A1 | 9/2010 | Feldstein et al. |
| 2010/0278757 | A1 | 11/2010 | Feldstein et al. |
| 2012/0014934 | A1 | 1/2012 | Altaffer et al. |
| 2012/0189553 | A1 | 7/2012 | Hier |
| 2012/0225022 | A1 | 9/2012 | Hier et al. |
| 2012/0263812 | A1 | 10/2012 | Commo |
| 2016/0175242 | A1 | 6/2016 | Hier et al. |

FOREIGN PATENT DOCUMENTS

| | | |
|---|---|---|
| JP | 2001-190573 A | 7/2001 |
| JP | 2006-028152 A | 2/2006 |
| KR | 2010/0133107 A | 12/2010 |
| WO | WO 2010/014870 A2 | 2/2010 |
| WO | WO 2010/098854 A1 | 9/2010 |
| WO | WO 2012/009469 A2 | 1/2012 |
| WO | WO 2012/103264 A1 | 8/2012 |
| WO | WO 2014/043163 A1 | 3/2014 |

OTHER PUBLICATIONS

International Preliminary Report on Patentability for PCT/US2013/059135 dated Mar. 26, 2015.
[No Author Listed], Natracol Annatto Extract WSP. ROHA Coloring the Future. Dated Jul. 1, 2010. 3pages.
[No Author Listed], Plaque-A-Way Toothpaste. Proprietary Toothpaste Compounding Procedures and Proprietary Toothpaste Formulation. Northstar Intl. Dated Jul. 23, 2012. 2 pages.
[No Author Listed], Plaque-A-Way Toothpaste. Proprietary Toothpaste Formulation. Northstar Intl. Dated Jul. 31, 2012. 1 page.
[No Author Listed], Pomella Frequently Asked Questions. Pomella Product Information. 2014. Accessed online Apr. 2, 2015 at http://pomextract.com/frequently-asked-questions/. 2 pages.
Giuliano et al., To dye or not to dye: biochemistry of annatto unveiled. TRENDS in Biotechnology. vol. 21(12), Dec. 2003. pp. 513-516.
Glinsmann et al., Evaluation of health aspects of sugars contained in carbohydrate sweeteners. Report of Sugars Task Force. J Nutr. Nov. 1986;116(11 Suppl):S5-S16.
Kiefer, Disease prevention begins in the mouth. Life Extension magazine. Sep. 2008.
Lloyd, Punica Granatum. Western Druggist. Chicago, May 1897; pp. 2-9.
Martin, 6 nutritional benefits of organic carrots, May 29, 2012.
Mattousch et al., Caries lesions after orthodontic treatment followed by quantitative light-induced fluorescence: a 2-year follow-up. Eur J Orthod. Jun. 2007;29(3):294-8. Epub May 5, 2007.
Shannon et al., Prevention of decalcification in orthodontic patients by daily self-treatment with 0.4% SnF2 gel. Pediatr Dent. Jun. 1979;1(2):101-2.
Sukhia et al., Enamel decalcification in orthodontic patients. Pakistan Oral Dental J. Dec. 2008;28(2):193-197.
Werkman et al., 0492 Stain of four composite by the phytotherapic Punica granatum L., Metro Toronto Convention Centre Exhibit, 2008. 1 page.
U.S. Appl. No. 15/167,314, filed May 27, 2016, Hier et al.
Extended European Search Report dated Apr. 28, 2016 for Application No. 13836880.8.
[No Author Listed], Complementary colors. Wikipedia accessed online Nov. 29, 2016 at https://en.wikipedia.org/wiki/Complementary_colors. 9 pages.
U.S. Appl. No. 15/406,616, filed Jan. 13, 2017, Hier et al.
U.S. Appl. No. 15/282,183, filed Sep. 30, 2016, Hier et al.
U.S. Appl. No. 15/593,639, filed May 12, 2017, Hier et al.

* cited by examiner

DENTAL CLEANING COMPOSITION

RELATED APPLICATIONS

This application is a national stage filing under 35 U.S.C. § 371 of International Patent Application Ser. No. PCT/US2013/059135, filed Sep. 11, 2013, entitled "DENTAL CLEANING COMPOSITION", which claims the benefit under 35 U.S.C. § 119(e) of U.S. provisional application Ser. No. 61/699,640, filed Sep. 11, 2012, entitled "DENTAL CLEANING COMPOSITION", the entire contents of each of which are incorporated herein by reference.

FIELD OF THE INVENTION

This invention relates generally to plaque disclosing agents and also to dental cleaning compositions.

BACKGROUND ART

It is a well-accepted fact that dental plaque when allowed to accumulate on tooth surfaces can eventually lead to gingivitis, periodontal disease, caries and calculus. Thus, it is apparent that effective removal of deposits of dental plaque is absolutely essential for oral health. Accordingly, a proper oral hygiene practice which may be carried out by an individual on his or her own teeth or by a dentist, necessitates readily available means of identification and location of plaque deposits in the oral cavity. Since dental plaque is usually transparent and colorless and not easily visible, an individual frequently is not aware of the quantity or the location of dental plaque present in the mouth.

The prior art includes various dentifrices for removing plaque, including dentifricating paste, powders, and microbial liquids. As a general matter, these dentifrices contain a mixture of various ingredients including such materials as polishing agents and abrasives for scouring and scrubbing the teeth, and which are further operable, to some degree, to neutralize various acids present in the gaps between the teeth. These same substances further inhibit, to some extent, the subsequent growth of various forms of bacteria that contribute to the development of caries and other disorders. While the prior art dentifrices have varying degrees of success, they have not been successful in arresting decalcification and other diseases which are exasperated by the use of braces.

The amount of decalcification and tooth decay found in orthodontic patients, in fact, is alarming. Numerous studies have been conducted showing the severity of this problem in the orthodontic patient population. Each year, half of the three to five million yearly patients who get braces in the United States suffer from early tooth decay.

Accordingly, dye indicators for dental plaque as a means of measuring tooth cleanliness and to effect proper oral hygiene practices, have been widely explored in the prior art.

U.S. publication 2007 0237726 ('726 publication") teaches plaque disclosing products containing coloring agents or pigments that are absorbed by the plaque and render it visible. According to the '726 publication: "Most plaque disclosing compositions are based on colorants such as disclosed in U.S. Pat. Nos. 3,309,274; 3,624,219; 3,997,658; 4,302,439; 4,459,277; 4,517,172; 4,590,061; 4,666,700; 4,992,256; 5,098,691; 5,190,743; 7,182,935. Examples include synthetic organic colorants such as, amongst others, erythrosin (FD&C Red #3), Allura Red (FD&C Red #40), Green #8, Red #19, Red #22, Red #28, fluorescein (Yellow #7) and fluorescein disodium salt (Yellow #8).

The 726 publication teaches that natural colorants have been used as plaque disclosing agents, including a red dye extracted from sugar beet, a salt of sanguinarine, and cobalamin compounds, particularly cyanobalamin (Vitamin B12). According to the '726 publication, some of these colorants are invisible to the human eye in normal daylight or artificial light and may require the use of light of a particular wavelength to become visible.

U.S. Pat. No. 7,182,935 also discloses that natural colorants have been suggested as alternatives to the use of synthetic organic colorants as plaque disclosing agents. According to the '935 patent, artificial colorants have disadvantages which natural colorants do not present. "Some artificial colorants provoke diseases of the thyroid, lesions of the liver, hyperacidity and allergies such as, for example, asthma, rhinitis and rashes."

According to the '935 patent, examples of natural colorants used to disclose bacterial plaque are taught in U.S. Pat. No. 4,431,628 and U.S. Pat. No. 4,517,172. "The U.S. Pat. No. 4,431,628 refers to a method for indicating the presence of bacterial plaque, comprising an efficient quantity of natural colorant extracted from sugar beet. . . . U.S. Pat. No. 4,517,172 describes a method for the visualization of plaque, in such a manner that the plaque is visible to the naked eye under ultraviolet light. The method employs a salt of sanguinarine precipitated from extracts of plants selected from the group consisting of *Sanguinaria canadensis, Macleaya cordata, Corydalis sevctvozii, C. ledebouni, Chelidonium majus* and mixtures of these."

The '935 patent itself is directed to a disclosing agent based on natural colorants comprising at least one concentrated solution of natural colorant selected from the group consisting of colorants extracted from the aai (*Euterpe oleracea*) and colorants extracted from urucum seeds (also known as Annatto seeds) of the plant *Bixa orellana*.

It is believed that none of these prior art natural colorants have been commercially successful. It is believed that the reason for the lack of success is that these coloring agents are not visible enough, concentrated enough, appealing visually, and/or stable enough to comprise an effective product. It would be desirable to have a colorant that can be used safely and effectively in a dentifrice identifying plaque without the need for a UV light source.

SUMMARY OF THE INVENTION

The present invention relates to oral compositions for identifying plaque located in a person's mouth comprising a natural dental disclosing agent composition for revealing the presence of dental plaque in a person's mouth. It has been discovered, unpredictably, that the combination of a natural colorant in annatto seeds together with a blue colorant is superior to other colorants in disclosing plaque. The inventors tested more than forty different dye substances for their capacity to disclose plaque and then tested numerous combinations in an attempt to find a suitable disclosing agent that would (i) employ natural dye substances to the extent possible, (ii) be easily visible in situ, (iii) be safe at the concentrations needed for easy visualization, (iv) be appealing visually such that it would be likely to be accepted and used, and (v) be stable in a dentifrice for storage. Surprisingly, the blue colorant when combined with the natural colorant found in annatto seeds resulted in a dye with the characteristics sought by the inventors. The combination disclosed plaque in situ with a better contrast than either colorant alone, easily visible in situ. The combination in addition is a desirable mint green, providing the dentifrice itself with a color believed to be appealing to the public. Finally, in the presence of appropriate preservatives, the combination was stable in dental compositions, such as tooth-paste, making it suitable for commercial application.

Thus, according to one aspect of the invention, an oral compositions for identifying plaque located in a person's mouth is provided. The composition comprises a natural colorant in annatto seeds and a colorant that stains plaque and when added to annatto seed extract results in a color having a wave length of 500 nm to 580 nm, preferably 505 nm-535 nm. In one embodiment, the annatto seed extract is prepared by water-alkaline extraction. In one embodiment, the annatto seed extract is by weight approximately 3:1 parts carbohydrate and fat.

In one embodiment, the disclosing agent is an annatto seed extract and a blue colorant. In one embodiment the blue colorant is FD&C Blue No. 1. In another embodiment, the colorant is FD&C Blue #2. In one embodiment the colorant is purple carrot extract having a color strength in a 1% aqueous solution (E1%, 1% by weight) of 11.5-12.5 at a wave length of 425.

In one embodiment, the annatto seed extract is present in an amount between 0.1% and 3.0% w/w and the blue colorant is present in an amount between 0.02 and 1.25% w/w. In one embodiment, the annatto seed extract is present in an amount between 0.5% and 2.5% w/w and the blue colorant is present in an amount between 0.1 and 1.0% w/w. In one embodiment, the annatto seed extract is present in an amount between 1.5% and 2.0% w/w and the blue colorant is present in an amount between 0.2 and 0.3% w/w.

In another embodiment the annatto seed extract is combined with the natural colorant in purple carrots. In this case, the disclosing agent is made entirely from natural substances. In one embodiment, the annatto seed extract is combined with a purple carrot extract present in an amount of between 0.1%-5.0%. In one embodiment, the annatto seed extract is present in an amount between 0.1% and 3.0% w/w and the purple carrot extract is present in an amount between 0.1 and 5.0% w/w. In one embodiment, the annatto seed extract is present in an amount between 0.5% and 2.5% w/w and the purple carrot extract is present in an amount between 1.0 and 4.0% w/w. In one embodiment, the purple carrot extract is prepared by spray drying. In one embodiment, the purple carrot extract comprises by weight approximately equal parts carbohydrate and sugar.

The colorant may be any colorant that stains plaque and that when combined with the annatto seed extract results in a green color having a wave length of between about 500 nm and 580 nm. In one embodiment the combination results in a mint green color having a wave length of between 505 nm and 535 nm. In one embodiment the disclosing agent is annatto seed extract, purple carrot extract and blue colorant such as FD&C #1 or #2.

Advantageously, the addition of the colorant to the annatto seed extract reduces the amount of annatto seed extract necessary to achieve easy identification of plaque in situ.

The disclosing agent may optionally include one or more additional colorants, provided the overall color is within the designated wave length range. For example, it may include natural colorants such as from beets, pomegranates, and tomatoes. Such natural colorants can be extracts or concentrates, such as a purple carrot extract, a red beet extract, a pomegranate concentrate, and a tomato extract (e.g., lycopene). Likewise, it may include FD&C Orange #5, FD&C Red #3, FD&C Red #40, FD&C Green #3, FD&C Yellow #5, FD&C Yellow #6, b-Carotene, Mica based pearlecent pigments, Caramel, and/or Chlorophyllin Copper Complex (Including Potassium Copper Chlorophyllin). However, when other colorants are included, they should be added if at all only in combinations that preserve the desirable features of the invention, that is, desirable in situ contrast, an overall desirable mint green color, and stability in dental compositions, such as tooth-paste.

In any of the foregoing embodiments, the disclosing agent may be a component of a dental disclosing agent delivery composition, such as tooth paste, for delivering the dental disclosing agent to a person's mouth.

In any of the foregoing embodiments, the oral compositions for identifying plaque located in a person's mouth can comprise a stannous fluoride (and/or other stannous salts). In any of the foregoing embodiments, the oral compositions for identifying plaque located in a person's mouth can comprise 5-chloro-2-(2,4-dichlorophenoxy)phenol(triclosan), provided that it is preferred that stannous fluoride and triclosan are not employed in the same dentifrice. Such compositions are particularly beneficial for use by orthodontic patients. The present invention thus provides a method for effective delivery of stannous-containing or triclosan-containing compositions with effective tartar control by administering to a subject a stable dentifrice composition comprising a clinically effective amount of stannous-containing or triclosan-containing compositions in combination with a disclosing substance to highlight areas to be cleaned.

It is believed that the oral compositions of the invention are safe to use and prevent possible harm associated with using colorants as a source of dental disclosing agents.

In one embodiment, the oral composition is for identifying plaque located in a person's mouth which significantly reduces the amount of decalcification in orthodontic patients.

It is believed that the time involved for any patient is dental care will be greatly reduced, resulting in better compliance and success for the patients.

One aspect of the invention is a composition and a method of treatment for delivering a dental disclosing agent to a person's mouth that lets the patient see, immediately while brushing, where there is plaque build-up on their teeth. Once the stain is removed during the brushing process, the teeth are clean and the risk of decalcification is minimized. In one embodiment, the invention combines a significant concentration of stannous fluoride (which increases the strength of the tooth enamel and reduces the risk of decay), in conjunction with a disclosing agent that lets the patient see immediately while brushing, where there is plaque build-up on their teeth. Once the stain is removed during the brushing process, the teeth are clean and the risk of decalcification is minimized.

In one aspect, the invention allows the patient to visually determine the amount of brushing necessary in view of the dental abrasive employed to maximize cleaning and minimizing dentin abrasion.

These and other features, aspects, and advantages of the present invention will become evident to those skilled in the art from the detailed description which follows.

DETAILED DESCRIPTION OF THE PREFERRED EMBODIMENT

This invention is an oral composition, in one aspect in the form of a toothpaste, that combines a dental disclosing agent composition for revealing the presence of dental plaque in a person's mouth, the disclosing agent including a blue colorant and a natural colorant derived from annatto seeds, and a dental disclosing agent delivery composition for delivering the dental disclosing agent to a person's mouth that lets the patient see, immediately while brushing, where there is plaque build-up on their teeth. Once the stain is removed during the brushing process, the teeth are clean and the risk of decalcification is minimized. This product will replace any other toothpaste the patient has been using, and is excellent for the entire family to use daily.

One of the two principal disclosing agents in the composition is an extract from annatto seeds, obtained from a species of Bixaceae. Bixaceae, or the achiote family, is a family of dicotyledonous plants. Bixaceae includes 3 genera and a total of 25 species. The best-known of the species in this family is the source of annatto, the achiote, which belongs to the type genus of the family. Achiote (*Bixa orellana*) is a shrub or small tree originating from the tropical region of the Americas. Annatto is extracted from the reddish pericarp which surrounds the seed of the achiote. The fat soluble color in the crude extract is called bixin, which can then be saponified into water soluble norbixin. Annatto seed contains 4.5-5.5% pigments, which consists of 70-80% bixin. The yellow to orange color is produced by the chemical compounds bixin and norbixin, which are classified as carotenoids. However, unlike beta-carotene, another well-known carotenoid, annatto based pigments are not vitamin A precursors. The more norbixin in an annatto extract, the more yellow it is; a higher level of bixin gives it a more orange shade. In one embodiment, the annatto extract is a product sold under the tradename Natracol Annatto Extract WSP, by Roha USA, LLC, St. Louis, Mo., 63110. Natracol Annatto Extract WSP is obtained from annatto seeds by using water-alkaline method of extraction. It is further spray dried to get a fine free flowing powder. The norbixin content is 4%+/−0.2%, the pH is >9, the material is water soluble and the ingredients are maltodextrin, annatto extract, and polysorbate 80.

The first colorant may be any colorant that stains plaque and that when combined with the annatto seed extract results in a color with a wave length of between 500 nm and 580 nm, preferably 505 nm and 535 nm. In one embodiment, the colorant is a blue colorant which, when combined with the annatto extract, results in a mint green color. In one embodiment, the blue colorant is FD&C Blue #1:

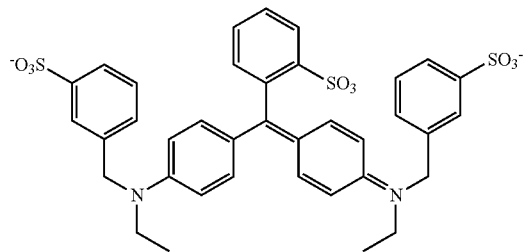

In another embodiment, the blue colorant is FD&C Blue #2.

In one embodiment the first colorant is the natural colorant in purple carrots. In one embodiment, the first colorant is a purple carrot extract. In one embodiment, the purple carrot extract is prepared by spray drying. In one embodiment, the purple carrot extract comprises by weight approximately equal parts carbohydrate and sugar. In one embodiment, the purple carrot extract comprised less than 1 percent (1%) by weight protein. In one embodiment, the purple carrot extract consists by weight approximately equal parts carbohydrate and sugar, and contains less than 1 percent (1%) by weight protein. In one embodiment, the purple carrot extract has a color strength in a 1% aqueous solution (E1%, 1% by weight) of 11.5-12.5 at a wave length of 425. One such extract is available from Roha USA, LLC, St. Louis, Mo., 63110.

Some synthetic dyes or artificial colorants have been linked to numerous diseases or illnesses, including asthma, thyroid tumors, depression and anxiety, attention deficient disorders, particularly in children. In addition, several synthetic dyes or artificial colorants are thought to be carcinogenic. In fact, several European countries have banned the use of some of these synthetic dyes or artificial colorants. While the research as to the harmful effects for some of these dyes may not be conclusive, the instant invention overcomes the risk of the harmful effect of certain colorants.

As used herein, the term "natural colorants" describes colorants, such as lakes, dyes, chemicals, including but not limited to phytochemicals, pigments, derived from or extracted from plants, algae, spices, herbs, or food sources, including but not limited to fruits and vegetables.

Accordingly, a dental disclosing agent used in the instant invention must be capable of adequately penetrating the plaque deposit and stain the plaque so as to be readily visible to the user, without producing an excessively prolonged staining effect. This staining efficacy must be selective so as to identify the areas of plaque-formation on all tooth surfaces and not stain gingival or other oral tissues. This selective staining efficacy must be coupled with easy removability from the mouth by simply brushing, washing, or rinsing after use. In addition, the taste must be pleasant and acceptable to the user, and the color must be pleasing. Lastly, it must be harmless and non-toxic.

The oral composition of the present invention includes a dental disclosing agent delivery composition which is made up of various ingredients, both active and inactive ingredients, which are capable of being mixed together in the form of a toothpaste for delivering the dental disclosing agent to the oral cavity and for providing various teeth cleaning and maintenance functionality. While the oral composition is preferably formulated as a toothpaste, other means of delivery, such as gels or liquids can be formulated.

In some embodiments, the dental disclosing agent delivery composition includes surfactants. Suitable non-limiting representatives of surfactants may include sulfated butyl oleate, medium and long chain fatty acid esters, sodium oleate, salts of fumaric acid, potassium glomate, organic acid esters of mono- and diglycerides, stearyl monoglyceridyl citrate, succistearin, dioctyl sodium sulfosuccinate, glycerol tristearate, lecithin, hydroxylated lecithin, sodium lauryl sulfate, sodium dodecyl sulphate, ammonium lauryl sulfae, acetylated monoglycerides, succinylated monoglycerides, monoglyceride citrate, ethoxylated mono- and diglycerides, sorbitan monostearate, calcium stearyl-2-lactylate, sodium stearyl lactylate, lactylated fatty acid esters of glycerol and propylene glycerol, glycerol-lactoesters of $C_8$-$C_{24}$ fatty acids, polyglycerol esters of $C_8$-$C_{24}$ fatty acids, propylene glycol alginate, sucrose $C_8$-$C_{24}$ fatty acid esters, diacetyl tartaric and citric acid esters of mono- and diglycerides, triacetin, sarcosinate surfactants, isethionate surfactants, tautate surfactants, pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures thereof In some embodiments, the dental disclosing agent delivery composition includes a fluoride source as fluoride is known to prevent tooth decay and makes teeth stronger as it incorporates itself into teeth enamel. Fluoride compounds have found widespread usage as effective ingredients for inhibiting dental caries. Among those fluoride compounds, fluoride salts which contain stannous ions (e.g. stannous fluoride) have been reported to cause an increase in the fluoride uptake by the dental enamel and consequently in acid-resistance of the enamel after treatment as compared with fluoride salts which do not contain stannous ions. U.S. Pat. No. 3,105,798 discloses a dentifrice composition consisting essentially of a water-soluble fluoride salt, stannous tin and a water-soluble source of six carbon aldonate groups capable of forming water-soluble complexes with stannous tin, the molar ratio of the aldonate group to stannous tin being in the range of from about one:one to about three:one, the molar ratio of stannous tin to fluoride ions being greater than one:one, said dentifrice having a pH of from about 5 to 7. Crystals of sodium pentafluorostannite ($NaSn_2F_5$) obtained by reacting one mole of sodium fluoride with two moles of stannous fluoride are described in U.S. Pat. No. 3,490,866. The use of stannous salts of polyphosphonic acids such as methanediphosphonic acid or ethane-1-hydroxy-1, 1-diphosphonic acid described in U.S. Pat. No. 3,549,677. The prior art compositions containing stannous ions and fluoride ions are effective to some extent for dental caries reduction, but their effectiveness is not so extremely high. Moreover, they require repeated application because of their lower reactivity to the tooth surface upon application or readily decreased retention of effectiveness.

Suitable non-limiting representative forms of fluoride include sodium monofluorophosphate, sodium fluoride, and stannous fluoride. Stannous fluoride is commonly incorporated into toothpastes for therapeutic efficacy in the control of dental caries. Stannous fluoride gels, rinses, and dentifrices have since been shown to provide clinical efficacy for the reduction of dental caries, dentinal hypersensitivity, dental plaque and gingivitis. In addition to these clinical effects, formulations containing stannous fluoride may also help to provide improved breath benefits through chemical and antibacterial actions.

In some embodiments, the dental disclosing agent delivery composition includes abrasives. Suitable non-limiting representative abrasives include silicas, aluminas, phosphates, carbonates and combinations thereof. In some embodiments, the abrasive agent is a silica selected from: precipitated silica, silica gels and combinations thereof. Moreover, in some embodiments the abrasive agent is selected from the following: calcium carbonate, sodium bicarbonate, sodium metaphosphate, potassium metaphosphate, tricalcium phosphate, dicalcium phosphate, dehydrated dicalcium phosphate, calcium hydrogen orthophosphate, and combinations thereof.

Hydrated silica is used as a dental abrasive to maximize cleaning and minimizing tooth abrasion. The ability to optimize such characteristics in the past has been limited generally to controlling the structures of the individual components utilized for such purposes for there has been no way of determining how along an individual should be brushing. For instance, if the teeth are clean then the use of a dental abrasive is of no effect toward the cleaning and may actually be harmful. However, if the teeth are unclean then the use of a dental abrasive is necessary to effectively remove the foreign particles. Prior art was limited to improving the dental abrasive and no teaching was directed to determining how much abrasion contact was necessary. The instant invention allows the consumer to visually determine the amount of brushing required, namely the brushing must be continued until all disclosing material is removed. Examples of modifications in precipitated silica structures for such dentifrice purposes are described in the art within such publications as U.S. Pat. Nos. 3,967,563, 3,988,162, 4,420,312, and 4,122,161 to Wason, U.S. Pat. Nos. 4,992,251 and 5,035,879 to Aldcroft et al., U.S. Pat. No. 5,098,695 to Newton et al., and U.S. Pat. Nos. 5,891,421 and 5,419,888 to McGill et al. Modifications in silica gels have also been described within such publications as U.S. Pat. No. 5,647,903 to McGill et al., U.S. Pat. No. 4,303,641, to DeWolf, II et al., U.S. Pat. No. 4,153,680, to Seybert, and U.S. Pat. No. 3,538,230, to Pader et al. Such disclosures teach improvement in such silica materials in order to impart increased cleaning capacity and reductions in dentin abrasion levels for dentifrice benefits. However, these improvements lack the ability to deliver preferred property levels that accord a dentifrice producer the ability incorporate such an individual material in different amounts with disclosure components in order to effectuate different resultant levels of such cleaning and abrasion characteristics. Silica combinations involving compositions of differing particle sizes and specific surface areas are disclosed in U.S. Pat. No. 3,577,521. to Karlheinz Scheller et al., U.S. Pat. No. 4,618,488 to Macyarea et al., U.S. Pat. No. 5,124,143 to Muhlemann, and U.S. Pat. No. 4,632,826 to Ploger et al. Such resultant dentifrices, however, fail to provide desired levels of abrasion and cleaning simultaneously by use of a visual indicator. The instant invention combines the use of a dental disclosing agent, a fluoride ion, and a dental abrasive within a single paste.

In some embodiments, the dental disclosing agent delivery composition includes humectants such as, but not limited to, water, sorbitol, glycerine, xylitol, or combinations thereof.

In some embodiments, the dental disclosing agent delivery composition includes thickeners. Suitable non-limiting representative thickeners include, methyl cellulose, alginates, carrageenan, xanthan gum, gelatin, carob, tragacanth, locust bean, and carboxy methyl cellulose, cellulose gum, acidulants such as malic acid, adipic acid, citric acid, tartaric acid, fumaric acid, and mixtures thereof In some embodiments, the dental disclosing agent delivery composition includes preservatives. Suitable non-limiting representative preservatives include sodium benzoate, ethyl paraben, methyl paraben, and combinations thereof.

In some embodiments, the dental disclosing agent delivery composition includes flavoring agents. Suitable non-limiting representatives flavoring those flavors known to one of skill in the art, such as natural and artificial flavors, and include synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, and fruit essences including apple, pear, peach, grape, strawberry, raspberry, cherry, plum, pineapple, apricot, aldehyde flavorings, and combinations thereof.

In some embodiments, the dental disclosing agent delivery composition includes sweeteners. Suitable non-limiting representatives sweeteners include selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Illustrative examples include soluble saccharin salts, i.e., sodium or calcium saccharin salts, ihydrochalcones, monellin, steviosides, glycyrrhizin, dihydroflavenol, and sugar alcohols such as sorbitol, mannitol, maltitol, and L-aminodicarboxylic acid aminoalkenoic acid ester amides.

In some embodiments, the dental disclosing agent delivery composition includes vitamins, such as Vitamin E, alpha-tocopherol.

In some embodiments, the dental disclosing agent delivery composition includes antimicrobial agents/antibacterial agents. Suitable non-limiting representative antimicrobial agents/antibacterial agents include triclosan, xylitol, or cetylpyridium chloride employed alone or in combination thereof. The antibacterial agent extends the shelf life of the dental composition but can further minimize the microbial population in the mouth. Since the oral environment is conducive to microbial growth and subject to the reintroduction of food and microorganisms, and because plaque and calculus are continually being deposited on teeth, the composition must address the microbial growth during the cleaning process. Dental plaque which forms on tooth surfaces and restorations are colonies of harmful bacteria, which cannot be flushed away by simply rinsing with water. Active brushing of the teeth is required to remove the adherent plaque and the use of triclosan will destroy the harmful bacteria.

In some embodiments, the dental disclosing agent delivery composition includes chelating agents. Non-limiting chelating agents include pyrophosphates, triphosphates, polyphosphates, polyphosphonates, dialkali metal pyrophosphate salt, a tetra alkali, tetrasodium pyrophosphate, tetrapotassium pyrophosphate, sodium tripolyphosphate, polyphosphate salt, EDTA (ethylenediaminetetraacetate) and salts of EDTA such as calcium disodium ethylenediaminetetraacetate dehydrate, (CaNa$_2$EDTA.2H$_2$O, Calcium Disodium EDTA FCC) or disodium ethylenediaminetetraacetate dehydrate (Na$_2$H$_2$EDTA.2H$_2$O, Disodium EDTA FCC, Edetate Disodium USP), and combinations thereof. The use of EDTA, and its salts, either in the dental disclosing agent delivery composition or disclosing agent composition serves several functions. First, it will act as a plaque softening and degrading agent, aiding in the removal of plaque. The actual process would involve chelation of trace metals having multivalent ions, such as iron (Fe), copper (Cu), manganese (Mn), calcium (Ca), magnesium (Mg), or zinc (Zn). In addition, ETDA, and their salts, by chemically binding and effectively chelating the trace metals, minimizes the effects of the trace metals on the color, flavor, and shelf-life capacity.

In some embodiments, the dental disclosing agent delivery composition includes anti-tartar agents such as tetrasodium pyrophosphate.

The following tables are illustrative embodiments of the dental disclosing agent delivery composition and the dental disclosing agent composition. While Table 1 describes the dental disclosing agent delivery composition in the preferred embody form of a toothpaste, the disclosing agent delivery composition may be formulated in other forms, such as, but not limited to, gel or liquid formulations.

TABLE 1 is a general example of a dental disclosing agent delivery composition of the invention.

TABLE 1

| Component | Quantity % w/w |
|---|---|
| Dicalcium phosphate (calcium hydrogen orthophosphate) | 37.0-45.0% |
| Water | 5.0-25.0% |
| Sorbitol (D-Glucitol) | 10.0-20.0% |
| Glycerin | 8.0-20.0% |
| Tetrasodium pyrophosphate (TSPP) | 0.25-3.0% |
| Sodium lauryl sulphate (sodium dodecyl sulphate) | 0.5-2.0% |
| Sodium saccharin (1,2-Benzisothiazol-3(2H)-one, 1,1-dioxide, sodium salt) | 0.10-2.5% |
| Titanium dioxide | 0.0-1.5% |
| Dye Package, Annatto Extract, WSP | 0.5-2.5% |
| Dye Package, FD&C Blue No. 1 | 0.1-1.0% |
| Sodium benzoate | 0.0-3.0% |
| Cellulose gum (Carboxymethyl cellulose) | 0.5-4.0% |
| Alpha-tocopherol (Vitamin-E Natural) | 0-(0.5)% |
| Sodium Fluoride (Active ingredient) | 0.1-0.25% |
| Triclosan (2,4,4'-Trichloro-2'hydroxydiphenyl ether) | 0.0-3.0% |
| calcium disodium ethylenediaminetetraacetate dehydrate (CaNa$_2$EDTA•2H$_2$0, Calcium Disodium EDTA FCC) | 0.0-1.5% |
| disodium ethylenediaminetetraacetate dehydrate (Na$_2$H$_2$EDTA•2H$_2$0, Disodium EDTA FCC, Edetate Disodium USP) | 0.0-1.4% |

In Table 1, purple carrot extract present in an amount of between 0.1%-5.0% may be substituted for the FD&C Blue #1 or combined with the FD&C blue #1.

Table 2 illustrates a specific embodiment of a dental disclosing agent composition in accordance with the instant invention.

TABLE 2

| Component | Quantity % w/w |
|---|---|
| Dicalcium phosphate | 27.3% |
| Water | 29.65% |
| Sorbitol (D-Glucitol) | 19.75% |
| Glycerin | 13.0% |
| Sodium lauryl sulphate(sodium dodecyl sulphate) (30% soln.) | 4.5%% |
| Sodium saccharin (1,2-Benzisothiazol-3(2H)-one 1,1-dioxide, sodium salt) | 0.35% |
| Spearmint oil | 0.29% |
| Mint flavor, artificial | 0.40% |
| Titanium dioxide | Optional, 0-1.0% |
| Dye Package, Annatto Extract, WSP | 1.89% |
| Dye Package, FD&C Blue No. 1 | 0.1% |
| Sodium benzoate | 0.32% |
| Cellulose Gum | 0.18% |
| Alpha-Tocopherol (Vitamin E-Natural) | Optional, 0-0.5% |
| Sodium Fluoride (Active Ing.) | 0.25%(fluoride ion 0.15% w/v) |
| Tetrasodium pyrophosphate (TSPP) | 0.2% |
| *Triclosan (Active Ing.) *Will not be used in conjunction with Sodium Fluoride. (2,4,4'-Trichloro2'-hydroxydiphenyl ether) | Optional, 0-3.0% |
| calcium disodium ethylenediaminetetraacetate dihydrate (CaNa$_2$EDTA•2H$_2$0, Calcium Disodium EDTA FCC) | Optional, 0-1.5 |
| disodium ethylenediaminetetraacetate dihydrate (Na$_2$H$_2$EDTA•2H$_2$0, Disodium EDTA FCC, Edetate Disodium USP)Disodium USP) | 0.3% |
| Sodium hydroxide 50% soln. | Adjust pH to 6.2-7.0 |

The process for producing the dental disclosing agent delivery composition of the oral composition for identifying plaque located in a person's mouth in accordance with the instant invention is as follows:

Basic Compounding Process Outline

Phase-A
Mix Glycerin, Sorbitol and CMC, Combine with moderate agitation till clear (no lumps).
Phase-B
Add TSPP, Sodium Saccharin, Sodium Fluoride, and Sodium Benzoate and to water (Distilled or RO/DI) at 50-60 C., mix with moderate agitation till dissolved.
Add B into A with elevated agitation, mix till clear (no lumps) to give A/B.
Phase-C
Add sodium Fluoride solution to A/B. Phase-C
Phase-D
Add Dicalcium phosphate to A/B with elevated agitation till uniform. Slow and De-aerate completely.
Phase-E
Add SLS, dye package, and Flavor, mix with moderate agitation till uniform. Hold.

Basic Compounding Process Outline for Dye Package

There are two (2) phases for all Supplement/Dye packages:
Phase A: Add SLS, Sodium Benzoate and, to water at 40-50 C. mix till clear.
Phase B: Add to A all colorants, mix at low agitation till clear (Do not aerate), to form dye package.
*Add to backbone dye package as directed above at prescribed quantities at finished temp.
Final pH Adjustment:
Sample final product for Lab/R&D to check for pH level. If needed use predetermined amount of Sodium Hydroxide provided by Lab/R&D and add to batch under low speed agitation. Resample to ensure pH range of 6.2-7.0 is achieved.

It is to be understood that while a certain form of the invention is disclosed, it is not to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An oral composition for identifying plaque located in a person's mouth comprising:
a dental disclosing agent composition for revealing the presence of dental plaque in a person's mouth comprising a mixture of a blue colorant and an annatto seed extract prepared by water-alkaline extraction, wherein the annatto seed extract is present in an amount between 0.1% and 3.0% w/w and the blue colorant is present in an amount between 0.02% and 1.25% w/w, wherein the mixture produces a green color having a wave length of between 500 nm and 580 nm inclusive.

2. The oral composition for identifying plaque located in a person's mouth according to claim 1 wherein said blue colorant comprises FD&C Blue No. 1 or comprises FD&C Blue No. 2.

3. The oral composition for identifying plaque located in a person's mouth according to claim 1 wherein said dental disclosing agent composition further comprises sodium fluoride.

4. The oral composition for identifying plaque located in a person's mouth according to claim 1 wherein said dental disclosing agent delivery composition further comprises 5-chloro-2-(2,4-dichlorophenoxy) phenol (triclosan).

5. The oral composition for identifying plaque located in a person's mouth according to claim 1, further comprising one or more of surfactants, a fluoride source, abrasives, humectants, thickeners, preservatives, antimicrobial agents, flavoring agents, sweeteners, vitamins, and coloring agents.

6. The oral composition for identifying plaque located in a person's mouth according to claim 1 wherein said oral composition comprises at least one chelating agent.

7. The oral composition for identifying plaque located in a person's mouth according to claim 6 wherein said at least one chelating agent is selected from the group consisting of calcium disodium ethylenediaminetetraacetate dehydrate and disodium ethylenediaminetetraacetate dehydrate.

8. The oral composition for identifying plaque located in a person's mouth according to claim 1 wherein said oral composition comprises a flavoring.

9. The oral composition for identifying plaque located in a person's mouth according to claim 8 wherein said flavorings are derived from natural sources.

10. An oral composition for identifying plaque located in a person's mouth comprising:
a dental disclosing agent composition for revealing the presence of dental plaque in a person's mouth comprising:
a mixture of an annatto seed extract prepared by water-alkaline extraction and a blue colorant, wherein the annatto seed extract is present in an amount between 0.1% and 3.0% w/w and the blue colorant is present in an amount between 0.02% and 1.25% w/w, and wherein the mixture produces a green color having a wave length of between 500 nm and 580 nm inclusive;
a dental disclosing agent delivery composition for delivering said dental disclosing agent to a person's mouth, said delivery composition comprising dicalcium phosphate in a concentration of about 37.0% to about 45.0%, water in a concentration of about 5.0% to about 25.0%, sorbitol in a concentration of about 10.0% to about 20.0%, glycerin in a concentration of about 8.0% to about 20.0%, tetrasodium pyrophosphate in a concentration of about 0.25% to about 3.0%, sodium lauryl sulphate in a concentration of about 0.5% to about 2.0%, sodium saccharin in a concentration of about 0.10% to about 2.5%, titanium dioxide in a concentration of about 0.0% to about 1.5%, sodium benzoate in a concentration of about 0.0% to about 3.0%, cellulose gum in a concentration of about 0.5% to about 4.0%, alpha-tocopherol in a concentration of about 0.0% to about 0.5% to about 5.0%, sodium fluoride in a concentration of about 0.0% to about 0.25%, triclosan in a concentration of about 0.0% to about 3.0%, calcium di sodium ethylenediaminetetraacetate dehydrate in a concentration of about 0.0% to about 1.5%, and di sodium ethylenediaminetetraacetate dehydrate a concentration of about 0.0% to about 1.5.

11. The oral composition for identifying plaque located in a person's mouth according to claim 10 wherein the blue colorant is present in an amount between 0.1 and 1.0% w/w.

12. The oral composition for identifying plaque located in a person's mouth according to claim 1, wherein the mixture produces a green color having a wave length of between 505 nm and 535 nm inclusive.

13. The oral composition for identifying plaque located in a person's mouth according to claim 5, wherein the at least one preservative is sodium benzoate.

* * * * *